United States Patent [19]

Nakamori et al.

[11] 4,184,918

[45] Jan. 22, 1980

[54] METHOD FOR PRODUCING 4-FORMYL-2-AMINO-BUTYRIC ACID (GLUTAMIC SEMIALDEHYDE)

[75] Inventors: Shigeru Nakamori, Yokohama; Kenzo Yokozeki, Kawasaki; Koji Mitsugi, Yokohama, all of Japan

[73] Assignee: Ajinomoto Company Incorporated, Tokyo, Japan

[21] Appl. No.: 901,088

[22] Filed: Apr. 28, 1978

[30] Foreign Application Priority Data

May 2, 1977 [JP] Japan .................................. 52-50930

[51] Int. Cl.² ............................................. C12D 13/06
[52] U.S. Cl. ..................................... 435/106; 435/108; 435/842; 435/840
[58] Field of Search ............................... 195/47, 29, 30

[56] References Cited

PUBLICATIONS

Baich et al., Biochim. Biophysica Acta, vol. 104, pp. 397–404 (1965).
Berg et al., Journal of Bacteriology, Jun. 1974, vol. 118, pp. 928–939 (Jun. 1974).

*Primary Examiner*—Lionel M. Shapiro
*Attorney, Agent, or Firm*—Oblon, Fisher, Spivak, McClelland & Maier

[57] ABSTRACT

A method for producing 4-formyl-2-amino-butyric acid(FABA), which comprises: culturing a mutant capable of producing FABA and belonging to the genus Brevibacterium or Corynebacterium in a culture medium until a substantial amount of FABA has accumulated in the culture medium, and recovering the accumulated FABA from the culture medium.

6 Claims, No Drawings

METHOD FOR PRODUCING 4-FORMYL-2-AMINO-BUTYRIC ACID (GLUTAMIC SEMIALDEHYDE)

BACKGROUND OF THE INVENTION

1. Field of the Invention

This invention relates to a method for producing 4-formyl-2-amino-butyric acid (hereinafter referred to as FABA) by fermentation.

2. Description of the Prior Art

FABA can be used as a starting material for the production of tryptophan (Japanese Published Unexamined patent application No. 14661/1973.

As to the fermentation method for the production of FABA, it has been known that an L-proline requiring mutant of *Escherichia coli* (Biochim. Biophys. Acta., 104, 397, (1965)) or *Salmonera typhimurium* (J. Bacteriol., 118, 928 (1974)) produced FABA in the culture media, but the amounts of FABA accumulated in their culture media were not sufficiently high.

Therefore it is required to find and provide more economic method of obtaining FABA.

SUMMARY OF THE INVENTION

Very excellent FABA producing mutants have now been induced from the parent strains of the genus Brevibacterium and Corynebacterium, and is a method is now provided for producing FABA which comprises culturing a mutant capable of producing FABA and belonging to the genus Brevibacterium or Corynebacterium in a culture medium until a substantial amount of FABA is accumulated in the culture medium, and recovering the accumulated FABA from the culture medium.

According to the method of this invention only the L-isomer of FABA is produced, and then it is very convenient to use the L-FABA as the starting material of L-tryptophan production.

DETAILED DESCRIPTION OF THE PREFERRED EMBODIMENTS

The microorganisms used in the process of this invention are mutants from the parent strains of the genus Brevibacterium or Corynebacterium. The most preferred mutants are those requiring L-proline for their growth. Desirably, the mutants have additional characteristics given through mutation such as L-ornithine-requirement, and resistance to antagonists of L-proline such as 3,4-dehydro-proline or antagonists of L-arginine such as arginine hydroxamate.

Representative specimens of mutants capable of producing FABA are as follows:

*Brevibacterium flavum* AJ 11139 (FERM-P 4032), NRRL B-11,292.

*Brevibacterium lactofermentum* AJ 11243, NRRL B-11,293.

*Corynebacterium glutamicum* AJ 11244, NRRL B-11,294.

*Brevibacterium flavum* AJ 11245, NRRL B-11,295.

The first three specimens mentioned above are mutants requiring L-proline for growth, and the last specimen is a mutant requiring L-proline and L-isoleucine for growth, and resistant to 500γ/ml sulfaguanidine and 3,000γ/ml DL-3,4-dehydroproline.

The parent strains of the mutants of this invention belong to the genus Corynebacterium or Brevibacterium, and the most preferred parent strains are L-glutamic acid producing bacteria of the two genera such as

*Brevibacterium divaricatum* ATCC 14020,
*Brevibacterium flavum* ATCC 14067,
*Brevibacterium lactofermentum* ATCC 13869,
*Brevibacterium roseum* ATCC 13825,
*Brevibacterium saccharolyticum* ATCC 14066,
*Corynebacterium acetoacidophilum* ATCC 13870,
*Corynebacterium acetoglutamicum* ATCC 15806,
*Corynebacterium glutamicum*, and *Corynebacterium lilium* ATCC 15990

Conventional mutagenic techniques such as contacting the cells of the parent strains with N-methyl-N'-nitro-N-nitrosoguanidine can be applied for inducing the mutant strains of this invention from the parent strains as mentioned above.

The culture media in which the mutants of this invention are propagated are conventional themselves, and contain carbon sources, nitrogen sources, inorganic ions, and when required minor organic nutrients such as vitamins or amino acids. When L-proline requiring mutants are cultured, L-proline or compounds substitutive with L-proline are added to the culture medium.

Preferably the culture media contain further reducing agents such as $NaHSO_3$.

Preferred carbon sources are, for example, carbohydrates such as glucose, fructose, and sucrose; alcohols such as ethanol, glycerol, and sorbitol; and organic acids such as acetic acid and higher fatty acids. Suitable nitrogen sources include, for example, aqueous ammonia, gaseous ammonia, ammonium salts, and urea. As the inorganic ions, magnesium ions, calcium ions, ferrous ions, manganese ions, potassium ions, phosphate ions, and others are supplemented to the culture medium when it is preferred. When L-glutamic acid is added to the culture medium, the yield of FABA is sometimes increased.

The cultivation is carried out under aerobic conditions, adjusting the pH of the culture medium to pH 4 to 10, while maintaining the temperature of the medium at 20° to 40° C. After 20 to 100 hours of cultivation, FABA is accumulated in the culture medium.

FABA accumulated in the resultant culture liquid can be recovered in a conventional manner such as adsorption on cation exchange resin, and elution with 0.5 N HCl.

EXAMPLE 1

An aqueous culture medium was prepared such that it contained, per deciliter, 10 g glucose, 6.0 g $(NH_4)_2SO_4$, 0.1 g $KH_2PO_4$, 0.8 g $MgSO_4.7H_2O$, 1.0 mg $FeSO_4.7H_2O$, 1.0 mg $MnSO_4.4H_2O$, 45 μg biotin, 100 μg thiamine.HCl, 1.0 ml soybean-protein hydrolyzate, 25 mg L-proline, and 5 g $CaCO_3$, and was adjusted to pH 7.0 with KOH, 20 ml batches of the aqueous culture medium were placed in 500 ml shaking flasks and heated to sterilize.

Each of the mutants listed in Table 1 was inoculated in the medium, and cultured at 30° C. for 48 hours with shaking.

The amounts of FABA shown in Table 1 were found in the resultant culture liquids.

Table 1

| Mutants used | FABA accumulated (mg/ml) |
|---|---|
| AJ 11139 | 2.60 |
| AJ 11243 | 1.35 |

Table 1-continued

| Mutants used | FABA accumulated (mg/ml) |
|---|---|
| AJ 11244 | 1.28 |

EXAMPLE 2

The aqueous culture medium shown in Example 1 further contained 15 mg/dl L-isoleucine, and 10 g/dl glucose in the medium of Example 1 was replaced with 10 g/dl sucrose. *Brevibacterium flavum* AJ 11245 was cultured in this aqueous culture medium in the same manner as in Example 1.

After 24 hours of cultivation from the initiation, NaHSO$_3$ was added to the culture medium in the amount of 1 g/dl, and cultivation was continued for an additional 24 hours. In the resultant culture liquid, 15.0 mg/ml of FABA was accumulated.

One liter of the culture liquid of AJ 11245 was prepared in the same manner as mentioned above, and cells were removed by centrifugation from the culture liquid. The supernatant thus obtained was acidified to pH 2.0, evaporated to 300 ml, and passed through a column of "Dowex"-50X4 (H+).

The column was washed with water and then 0.01 N HCl, and FABA adsorbed on the resin was eluted with 0.5 N HCl. The eluate was dried and 10.3 g of FABA powder was obtained.

What is claimed is:

1. A method for producing 4-formyl-2-amino-butyric acid, which comprises: culturing a mutant capable of producing FABA and belonging to the genus Brevibacterium or Corynebacterium in a culture medium until a substantial amount of FABA has accumulated in the culture medium, and recovering the accumulated FABA from the culture medium.

2. The method of claim 1, wherein said mutant belongs to the species *Brevibacterium flavum, Brevibacterium lactofermentum* or *Corynebacterium glutamicum*.

3. The method of claim 1, wherein said mutant is *Brevibacterium flavum* NRRLB-11,292, *Brevibacterium lactofermentum* NRRL B-11,293, *Brevibacterium flavum* NRRLB-11,295, or *Corynebacterium glutamicum* NRRL B-11,294.

4. The method of claim 1, wherein said culture medium contains a reducing agent.

5. The method of claim 1, wherein said culture medium is adjusted to pH 4–10, and the temperature of said medium is maintained at from 20° to 40° C.

6. The method of claim 1, wherein said accumulated FABA is recovered from said culture medium by absorption on a cation exchange resin, followed by elution with dilute aqueous hydrochloric acid.

* * * * *